(12) United States Patent
Li et al.

(10) Patent No.: US 11,538,581 B2
(45) Date of Patent: Dec. 27, 2022

(54) MONITORING SYSTEM, DEVICE AND COMPUTER-IMPLEMENTED METHOD FOR MONITORING PRESSURE ULCERS

(71) Applicants: TAIPEI MEDICAL UNIVERSITY, Taipei (TW); TRIHEALTH ENTERPRISE INC., LIMITED, New Taipei (TW); VAST TECHNOLOGIES INC., New Taipei (TW)

(72) Inventors: Yu-Chuan Jack Li, Taipei (TW); Jack Hsiao, New Taipei (TW); Wei Chuan Liao, New Taipei (TW)

(73) Assignees: TAIPEI MEDICAL UNIVERSITY, Taipei (TW); TRIHEALTH ENTERPRISE INC., LIMITED, New Taipei (TW); VAST TECHNOLOGIES INC., New Taipei (TW)

( * ) Notice: Subject to any disclaimer, the term of this patent is extended or adjusted under 35 U.S.C. 154(b) by 174 days.

(21) Appl. No.: 16/790,775

(22) Filed: Feb. 14, 2020

(65) Prior Publication Data
US 2021/0257087 A1 Aug. 19, 2021

(51) Int. Cl.
*G16H 40/67* (2018.01)
*G16H 20/30* (2018.01)
(Continued)

(52) U.S. Cl.
CPC .............. *G16H 40/67* (2018.01); *G06N 5/04* (2013.01); *G06N 20/00* (2019.01); *G06T 7/0012* (2013.01);
(Continued)

(58) Field of Classification Search
CPC ........ G16H 20/30; G16H 20/60; G16H 40/67; G16H 50/20; G16H 10/60
See application file for complete search history.

(56) References Cited

U.S. PATENT DOCUMENTS

2012/0271654 A1 10/2012 Croghan et al.
2013/0090571 A1* 4/2013 Nourani ................. G16H 20/30
600/587
(Continued)

FOREIGN PATENT DOCUMENTS

CN 102822651 A 12/2012
CN 208285434 U 12/2018
(Continued)

OTHER PUBLICATIONS

Kaewprag, Pacharmon, et al. "Predictive models for pressure ulcers from intensive care unit electronic health records using Bayesian networks." BMC medical informatics and decision making 17.2 (2017): 81-91. (Year: 2017).*
(Continued)

*Primary Examiner* — Linh Giang Le
*Assistant Examiner* — Constantine Siozopoulos
(74) *Attorney, Agent, or Firm* — Birch, Stewart, Kolasch & Birch, LLP (57) ABSTRACT

The present disclosure provides monitoring system, device and computed-implemented method for monitoring pressure ulcers. The monitoring system and the device are configured to: capture at least one image corresponding to a user; retrieve the anamnesis data of the user; and determine a pressure ulcers condition result corresponding to the at least one image and the anamnesis data according a pressure ulcers prediction model.

14 Claims, 9 Drawing Sheets

(51) Int. Cl.
    *G16H 50/50*     (2018.01)
    *G16H 50/70*     (2018.01)
    *G16H 50/20*     (2018.01)
    *G06N 20/00*     (2019.01)
    *G16H 10/60*     (2018.01)
    *G16H 70/60*     (2018.01)
    *G06N 5/04*     (2006.01)
    *G06T 7/00*     (2017.01)

(52) U.S. Cl.
    CPC .............. *G16H 10/60* (2018.01); *G16H 20/30* (2018.01); *G16H 50/20* (2018.01); *G16H 50/50* (2018.01); *G16H 50/70* (2018.01); *G16H 70/60* (2018.01); *G06T 2207/30088* (2013.01)

(56) References Cited

U.S. PATENT DOCUMENTS

| | | | |
|---|---|---|---|
| 2015/0109442 A1* | 4/2015 | Derenne | H04N 7/185 |
| | | | 348/143 |
| 2019/0307405 A1 | 10/2019 | Terry et al. | |
| 2020/0060910 A1* | 2/2020 | Lightcap | A61G 7/0516 |
| 2021/0219873 A1* | 7/2021 | Receveur | G16H 40/63 |

FOREIGN PATENT DOCUMENTS

| | | |
|---|---|---|
| CN | 109157347 A | 1/2019 |
| CN | 110584911 A | 12/2019 |
| WO | 2017176667 A1 | 10/2017 |
| WO | 2019178583 A1 | 9/2019 |
| WO | WO-2021076628 A1 * | 4/2021 |

OTHER PUBLICATIONS

Office Action of corresponding Taiwan patent application No. 109104751 dated Aug. 30, 2021.

* cited by examiner

MONITORING SYSTEM, DEVICE AND COMPUTER-IMPLEMENTED METHOD FOR MONITORING PRESSURE ULCERS

TECHNICAL FIELD

The present disclosure relates generally to a monitoring system, a device and a computer-implemented method for monitoring user, more particularly, to a monitoring system, a device and a computer-implemented method for monitoring pressure ulcers of user.

BACKGROUND

Pressure ulcers are injuries to skin and tissue resulting from pressure on the skin. Pressure ulcers could happen to skin of the body, and often happen to skin that covers bony areas of the body.

Further, people having medical conditions, which may restrict their ability to change poses or positions, are most at risk of pressure ulcers. For example, pressure ulcers usually happened to the patients who spend most of their time in a bed or wheel chair.

Some Standard Operating Procedures (SOPs) for treating pressure ulcers are applied to the patients. However, because pressure ulcers are hard-to-heal wounds and each patient may have different medical conditions, every patient who has pressure ulcers needs special care and treatment.

SUMMARY

Some embodiments of the present disclosure provide a computer-implemented method for monitoring pressure ulcers. The computer-implemented method for monitoring pressure ulcers includes: capturing at least one image corresponding to a user; retrieving anamnesis data of the user; and determining a pressure ulcers condition result corresponding to the at least one image and the anamnesis data according a pressure ulcers prediction model.

Some embodiments of the present disclosure provide a monitoring system for monitoring pressure ulcers. The monitoring system includes an image capturing unit, a processor and a storing unit. The image capturing unit captures at least one image corresponding to a user. The storing unit stores anamnesis data of the user, a pressure ulcers prediction model and a program. When the program is executed, the program causes the processor to: retrieve the at least one image from the image capturing unit; retrieve the anamnesis data from the storing unit; and determine a pressure ulcers condition result corresponding to the at least one image and the anamnesis data according the pressure ulcers prediction model.

Some embodiments of the present disclosure provide a device for monitoring pressure ulcers. The device includes an image capturing unit, a processor, a storing unit and a network interface. The image capturing unit captures at least one image corresponding to a user. The storing unit stores a pressure ulcers prediction model and a program. When the program is executed, the program causes the processor to: retrieve the at least one image from the image capturing unit; retrieve the anamnesis data from a network interface via the network interface; and determine a pressure ulcers condition result corresponding to the at least one image and the anamnesis data according the pressure ulcers prediction model.

The foregoing has outlined rather broadly the features and technical advantages of the present disclosure in order that the detailed description of the disclosure that follows may be better understood. Additional features and advantages of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

A more complete understanding of the present disclosure may be derived by referring to the detailed description and claims when considered in connection with the Figures, where like reference numbers refer to similar elements throughout the Figures.

DETAILED DESCRIPTION

Embodiments, or examples, of the disclosure illustrated in the drawings are now described using specific language. It shall be understood that no limitation of the scope of the disclosure is hereby intended. Any alteration or modification of the described embodiments, and any further applications of principles described in this document, are to be considered as normally occurring to one of ordinary skill in the art to which the disclosure relates. Reference numerals may be repeated throughout the embodiments, but this does not necessarily mean that feature(s) of one embodiment apply to another embodiment, even if they share the same reference numeral.

It shall be understood that, although the terms first, second, third, etc. may be used herein to describe various elements, components, regions, layers or sections, these elements, components, regions, layers or sections are not limited by these terms. Rather, these terms are merely used to distinguish one element, component, region, layer or section from another element, component, region, layer or section. Thus, a first element, component, region, layer or section discussed below could be termed a second element, component, region, layer or section without departing from the teachings of the present inventive concept.

The terminology used herein is for the purpose of describing particular example embodiments only and is not intended to be limited to the present inventive concept. As used herein, the singular forms "a," "an" and "the" are intended to include the plural forms as well, unless the context clearly indicates otherwise. It shall be further understood that the terms "comprises" and "comprising," when used in this specification, point out the presence of stated features, integers, steps, operations, elements, or components, but do not preclude the presence or addition of one or more other features, integers, steps, operations, elements, components, or groups thereof.

Pressure ulcers are hard-to-heal wounds. Some Standard Operating Procedures (SOPs) for treating pressure ulcers are developed and applied to the patients who have pressure ulcers. However, since each patient may have different medical conditions, every patient who has pressure ulcers needs custom treatment for caring his/her pressure ulcers.

Figure 1:
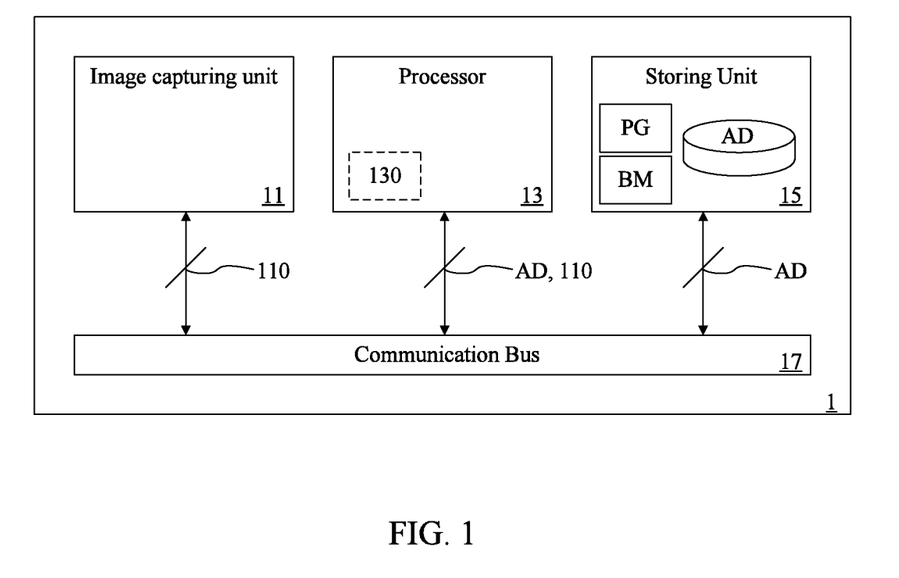
FIG. 1 is a block diagram of a monitoring system according to some embodiments of the present disclosure.

FIG. 1 illustrates a block diagram of a monitoring system 1 according to some embodiments of the present disclosure. The monitoring system 1 includes an image capturing unit 11, a processor 13 and a storing unit 15. In some embodiments, the image capturing unit 11, the processor 13 and the storing unit 15 are electrically coupled through a communication bus 17. The communication bus 17 may allow the image capturing unit 11 to transmit image data to the process 13, and may allow the processor 13 to execute a computer program PG stored in the storing unit 15.

The processor 13, the storing unit 15 and the computer program PG may be cooperatively configured to perform functions of the computer program PG. In other words, when executed, the computer program PG may generate one or more interrupts (e.g., software-interrupt) to cause the processor 13 and the storing unit 15 to perform functions of the computer program PG for monitoring pressure ulcers of user. The functions of the computer program PG will be further described hereinafter.

In some embodiments, when a user needs to be monitored for pressure ulcers, the image capturing unit 11 is disposed adjacent to the user for capturing at least one image 110 of the user. After capturing the at least one image 110 of the user, the image capturing unit 11 transmits the at least one image 110 to the processor 13.

In other words, the processor 13 retrieves the at least one image 110 from the image capturing unit 11. In the meantime, the processor 13 retrieves anamnesis data AD, which corresponds to the user, stored in the storing unit 15.

Next, in some embodiments, a pressure ulcers prediction model BM stored in the storing unit 15 is a machine learning model used for receiving images data and anamnesis data corresponding to user, and then predicting pressure ulcers condition change for user. Accordingly, the processor 13 determines, for the user, a pressure ulcers condition result 130 corresponding to the at least one image 110 and the anamnesis data AD according the pressure ulcers prediction model BM.

In some embodiments, the pressure ulcers condition result 130 may include different levels for indicating different predictions of the pressure ulcers condition of the user. For example, the pressure ulcers condition result 130 includes n number of levels which are specified as level "1" to level "n". When the pressure ulcers condition result 130 is determined as level "1", it means that the pressure ulcers condition of the user will become better. When the pressure ulcers condition result 130 is determined as level "n", it means that the pressure ulcers condition of the user will become worse.

Accordingly, a caregiver who cares for the user may treat the pressure ulcers of the user based on the pressure ulcers condition result 130. For example, the frequency of wound dressing may depend on the pressure ulcers condition result 130. When the pressure ulcers condition result 130 is determined as level "1", the frequency of wound dressing can be decrease. When the pressure ulcers condition result 130 is determined as level "n", the frequency of wound dressing should be increase.

In some embodiments, the pressure ulcers prediction model BM may include two phases for processing the data and generating the result. In detail, in the first phase, images corresponding to user are classified under different movement types corresponding to user. In the second phase, pressure ulcers condition result of user is determined according to movement type and anamnesis data of the user.

In particular, after the image capturing unit 11 captures the at least one image 110 corresponding to the user, the processor 13 determines a movement type corresponding to the at least one image 110 according to the first phase the pressure ulcers prediction model BM.

More specifically, the processor 13 retrieves the at least one image 110 and determines the movement type by the pressure ulcers prediction model BM. In other words, the processor 13 inputs the at least one image 110 to the first phase of the pressure ulcers prediction model BM for deriving the movement type as output data from the first phase of the pressure ulcers prediction model BM.

Then, the processor 13 determines the pressure ulcers condition result 130 corresponding to the movement type and the anamnesis data AD according the second phase of the pressure ulcers prediction model BM. In other words, the processor 13 inputs the movement type and the anamnesis data AD to the second phase of the pressure ulcers prediction model BM for deriving the pressure ulcers condition result 130 as output data from the second phase of the pressure ulcers prediction model BM.

In some embodiments, before determining the pressure ulcers condition result 130, movement frequency corresponding to the user may be introduced for more accurate result. In detail, the processor 13 determines a movement frequency according to the at least one image 110 corresponding to the user.

Then, according to the second phase of the pressure ulcers condition model BM, the processor 13 determines the pressure ulcers condition result 130 corresponding to the movement frequency, the movement type and the anamnesis data AD. In other words, the processor 13 inputs the movement frequency, the movement type and the anamnesis data AD to the second phase of the pressure ulcers prediction model BM for deriving the pressure ulcers condition result 130 as output data from the second phase of the pressure ulcers prediction model BM.

Before put to use, machine learning model of the disclosure may be generated and trained first. In detail, in some embodiments, the first phase of the pressure ulcers prediction model BM is configured to convert images corresponding to a user into information of movement types corresponding to the user, so that the first phase of the pressure ulcers prediction model BM is trained with a plurality of first data including images and movement types.

In particular, each first data includes a first training input data and a first training output data. The first training input data includes at least one training image. The first training output data includes a movement type which corresponds to the at least one training image.

Accordingly, the plurality of first data is used for training the first phase of the pressure ulcers prediction model BM to recognize images as movement type. In other words, the first phase of the pressure ulcers prediction model BM can be trained with the plurality of first data for converting images into movement types.

For example, training images corresponding to a user may be labeled as training movement types which include: turning over, feeding, changing intravenous drip position, massaging, wound cleaning, changing medical supply, etc.

Accordingly, after being trained with the training images and the training movement types, the first phase of the pressure ulcers prediction model BM is capable of classifying some captured images corresponding to the user under different movement types which include: turning over, feeding, changing intravenous drip position, massaging, wound cleaning, changing medical supply, etc.

To sum up, the first phase of the pressure ulcers prediction model BM is a trained machine learning scheme, that a data is inputted to the first phase of the pressure ulcers prediction model BM, and subsequently another data is outputted from the first phase of the pressure ulcers prediction model BM based on the inputted data. In some embodiments, the at least one image corresponding to the user is given as the input data for the first phase of the pressure ulcers prediction model BM, and the subsequent output data is the movement type.

It should be noted that, in some implementations, the first phase of the pressure ulcers prediction model BM may be established according to algorithms of You Only Look Once version 3 (YOLOv3) algorithm, Single Shot multiBox Detection (SSD) algorithm or Regions with Convolutional Neural Network (R-CNN) algorithm.

How to establish a machine learning scheme (i.e., the first phase of the pressure ulcers prediction model BM in some embodiments) by images and movement types based on YOLOv3 algorithm, SSD algorithm or R-CNN algorithm shall be appreciated by those skilled in the art based on the above disclosure, and thus will not be further described herein.

In some embodiments, the second phase of the pressure ulcers prediction model BM is configured to convert movement type, movement frequency and anamnesis data corresponding to the user into pressure ulcers condition result, so that the second phase of the pressure ulcers prediction model BM is trained with a plurality of second data including movement type, movement frequency and anamnesis data.

In particular, each second data includes a second training input data and a second training output data. The second training input data includes a training movement type, a training movement frequency and training anamnesis data. The second training output data includes a training pressure ulcers condition result which corresponds to the training movement type, the training movement frequency and the training anamnesis data.

Accordingly, the plurality of second data is used for training the second phase of the pressure ulcers prediction model BM to determine pressure ulcers condition result according to movement type, movement frequency and anamnesis data. In other words, the second phase of the pressure ulcers prediction model BM can be trained with the plurality of second data for converting movement type, movement frequency and anamnesis data into pressure ulcers condition result.

In some embodiments, each training pressure ulcers condition result may be judged by experienced doctors based on the corresponding training movement type, the training movement frequency and the anamnesis data.

In some embodiments, the anamnesis data is in text format and includes the factors which are determined as that may affect pressure ulcers conditions. For example, the anamnesis data includes at least one of disease type information, prescription information, medical test information, blood pressure information, body temperature information, diagnose information, medication use information, lab examination information, etc.

To sum up, the second phase of the pressure ulcers prediction model BM is a trained machine learning scheme, that a data is inputted to the second phase of the pressure ulcers prediction model BM, and subsequently another data is outputted from the second phase of the pressure ulcers prediction model BM based on the inputted data. In some embodiments, the movement type, the movement frequency and the anamnesis data corresponding to the user is given as the input data for the second phase of the pressure ulcers prediction model BM, and the subsequent output data is the pressure ulcers condition result.

It should be noted that, in some implementations, the second phase of the pressure ulcers prediction model BM may be established according to Deep Neural Networks (DNN) algorithm. How to establish a machine learning scheme (i.e., the second phase of the pressure ulcers prediction model BM in some embodiments) by the movement types, the movement frequencies, the anamnesis data and the pressure ulcers condition results based on DNN algorithm shall be appreciated by those skilled in the art based on the above disclosure, and thus will not be further described herein.

In some embodiments, the pressure ulcers prediction model BM may be a self-learning machine learning model. In detail, the input data (e.g., images corresponding to the user) and the output data (e.g., pressure ulcers condition result according to these images corresponding to the user) from the pressure ulcers prediction model BM can be respectively used as the training input data and the training output data for training the pressure ulcers prediction model BM.

Figure 2:
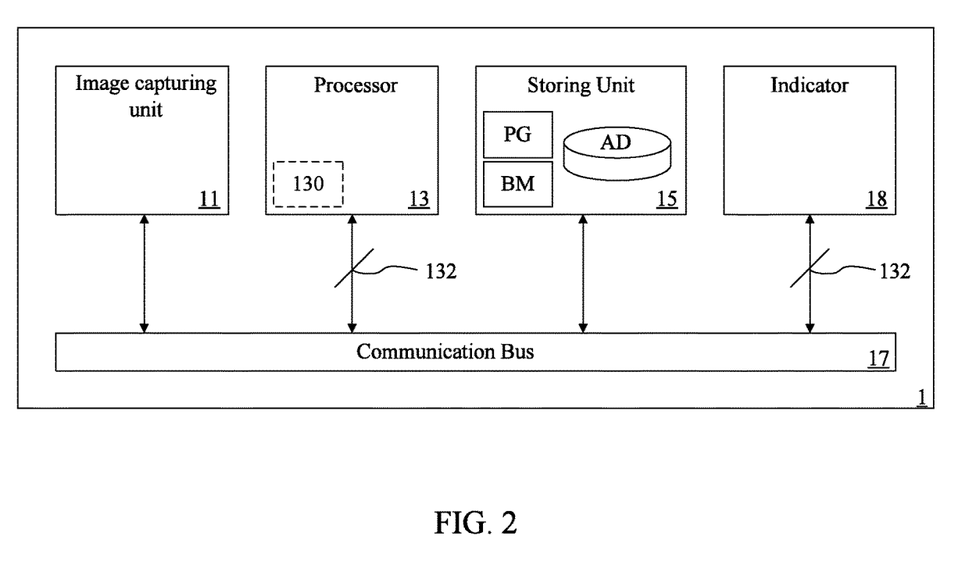
FIG. 2 is a block diagram of a monitoring system according to some embodiments of the present disclosure.

FIG. 2 illustrates a block diagram of the monitoring system 1 according to some embodiments of the present disclosure. In some embodiments, the monitoring system 1 further includes an indicator 18. After the processor 13 determines the pressure ulcers condition result 130, the processor 13 transmits a signal 132 to trigger the indicator 18 for informing a caregiver of the pressure ulcers condition result 130 so that the caregiver may apply a custom plan for the user.

In some embodiments, the indicator 18 may include a display. The signal for triggering the display may include text information and the display shows the text information. In some embodiments, the indicator 18 may include a light which can emit different color of lights for indicating different conditions. For instance, red light means the pressure ulcers condition will become worse, and the green light means the pressure ulcers condition will become better.

Figure 3:
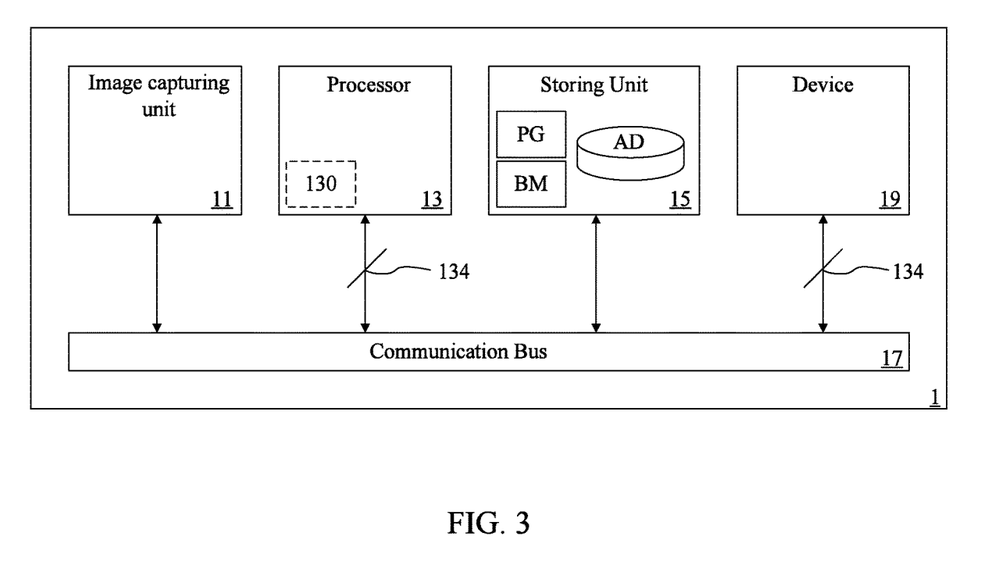
FIG. 3 is a block diagram of a monitoring system according to some embodiments of the present disclosure.

FIG. 3 illustrates a block diagram of the monitoring system 1 according to some embodiments of the present disclosure. In some embodiments, the monitoring system 1 further includes a device 19. After the processor 13 determines the pressure ulcers condition result 130, the processor 13 transmits a control signal 134 to control the device 19 for adjusting the positions of the user.

In some embodiments, the device 19 may include an electric mattress which is capable of adjusting the positions of the user. The control signal 134 may be used for controlling an angle or an air inflation status of the electric mattress.

Figure 4:
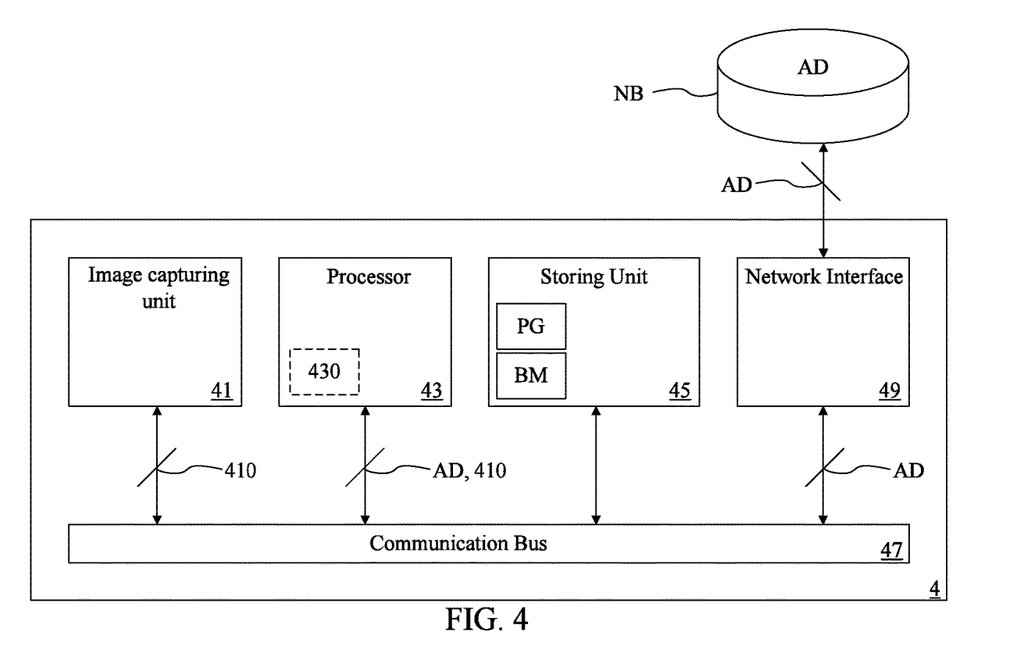
FIG. 4 is a block diagram of a device according to some embodiments of the present disclosure.

FIG. 4 illustrates a block diagram of a device 4 according to some embodiments of the present disclosure. In some embodiments, the device 4 includes an image capturing unit 41, a processor 43, a storing unit 45 and a network interface 49. In some embodiments, the image capturing unit 41, the processor 43, the storing unit 45 and the network interface 49 are electrically coupled through a communication bus 47. The communication bus 47 may allow the image capturing unit 41 to transmit image data to the process 43, and may allow the processor 43 to execute the computer program PG stored in the storing unit 45.

The processor 43, the storing unit 45 and the computer program PG may be cooperatively configured to perform the functions of the computer program. In other words, when executed, the computer program PG may generate one or more interrupts (e.g., software-interrupt) to cause the processor 43 and the storing unit 45 to perform functions of the computer program PG for monitoring pressure ulcers of user. The functions of the computer program PG will be further described hereinafter.

In some embodiments, the device 4 may be disposed adjacent a user, and the image capturing unit 41 may capture at least one image 410 of the user. After capturing the at least one image 410, the image capturing unit 41 transmits the at least one image 410 to the processor. In other words, the processor 43 retrieves the at least one image 410 from the image capturing unit 41.

In some embodiments, the processor 43 of the device 4 retrieves the anamnesis data AD from the network database NB via the network interface 49. Next, the processor 43 determines a pressure ulcers condition result 430 corresponding to the at least one image 410 and the anamnesis data AD according the pressure ulcers prediction model BM stored in the storing unit 45.

It should be noted that, in some embodiments, the device 4 may be an image capturing device with higher computing ability so that the image capturing device can monitor the user for determining pressure ulcers condition result 430 while the anamnesis data AD corresponding to the user is retrieved from the network database NB.

Figure 5:
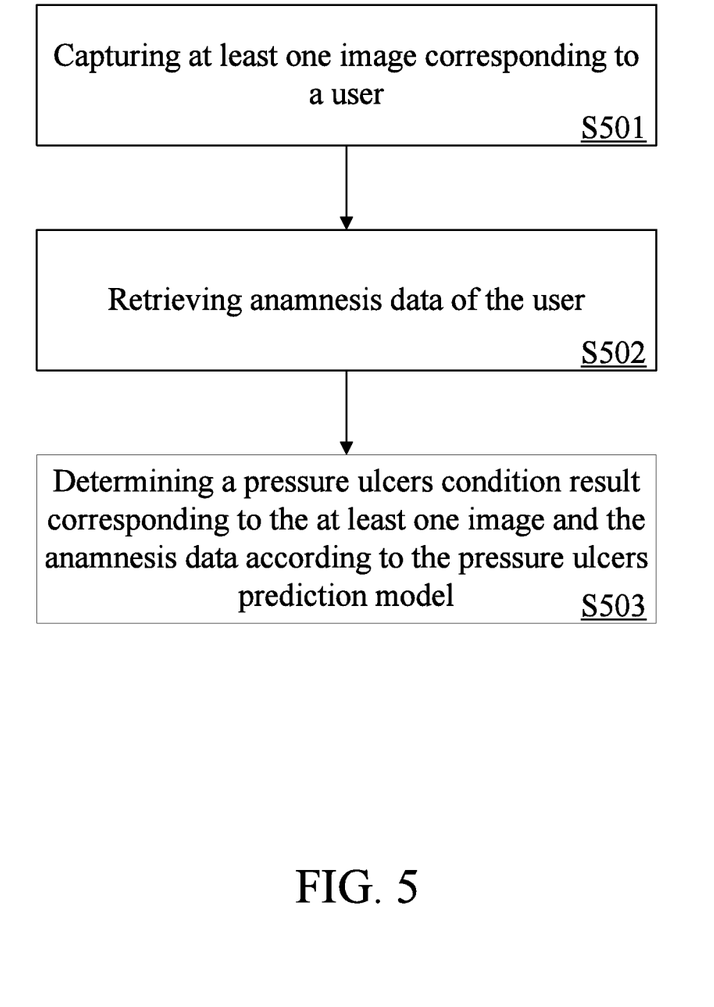
FIG. 5 is a flowchart diagram of a computer-implemented method for monitoring pressure ulcers according to some embodiments of the present disclosure.

Some embodiments of the present disclosure include a computer-implemented method for monitoring pressure ulcers, and a flowchart diagram thereof is shown in FIG. 5. The computer-implemented method of some embodiments is for use in a monitoring system (e.g., the monitoring system 1 of the aforesaid embodiments). Detailed steps of the computer-implemented method are described below.

Step S501 is executed, by an image capturing unit of the monitoring system, to capture at least one image corresponding to a user. Step S502 is executed, by a processor of the monitoring system, to retrieve anamnesis data of the user. The anamnesis data is stored in a storing unit of the monitoring system.

In some embodiments, a pressure ulcers prediction model stored in the storing unit is a trained machine learning scheme that image data and anamnesis data corresponding to the user are inputted to the pressure ulcers prediction model, and subsequently pressure ulcers condition result is outputted from the pressure ulcers prediction model based on the inputted data.

Accordingly, Step S503 is executed, by the processor, to determine a pressure ulcers condition result corresponding to the at least one image and the anamnesis data according to the pressure ulcers prediction model. The pressure ulcers condition result may include different levels for indicating different predictions of the pressure ulcers condition of the user.

Figure 6A:
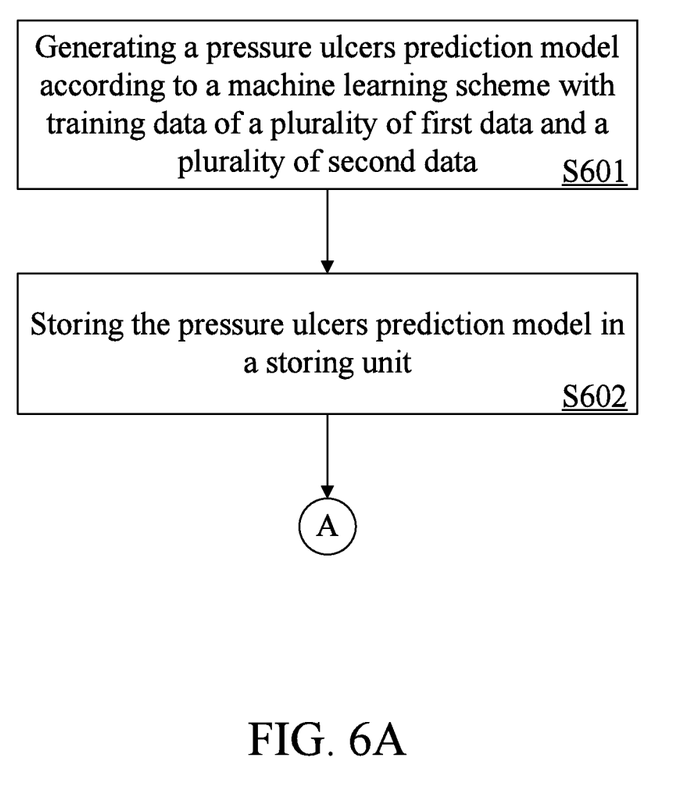
FIGS. 6A to 6C are flowchart diagrams of a computer-implemented method for monitoring pressure ulcers according to some embodiments of the present disclosure.
Figure 6B:
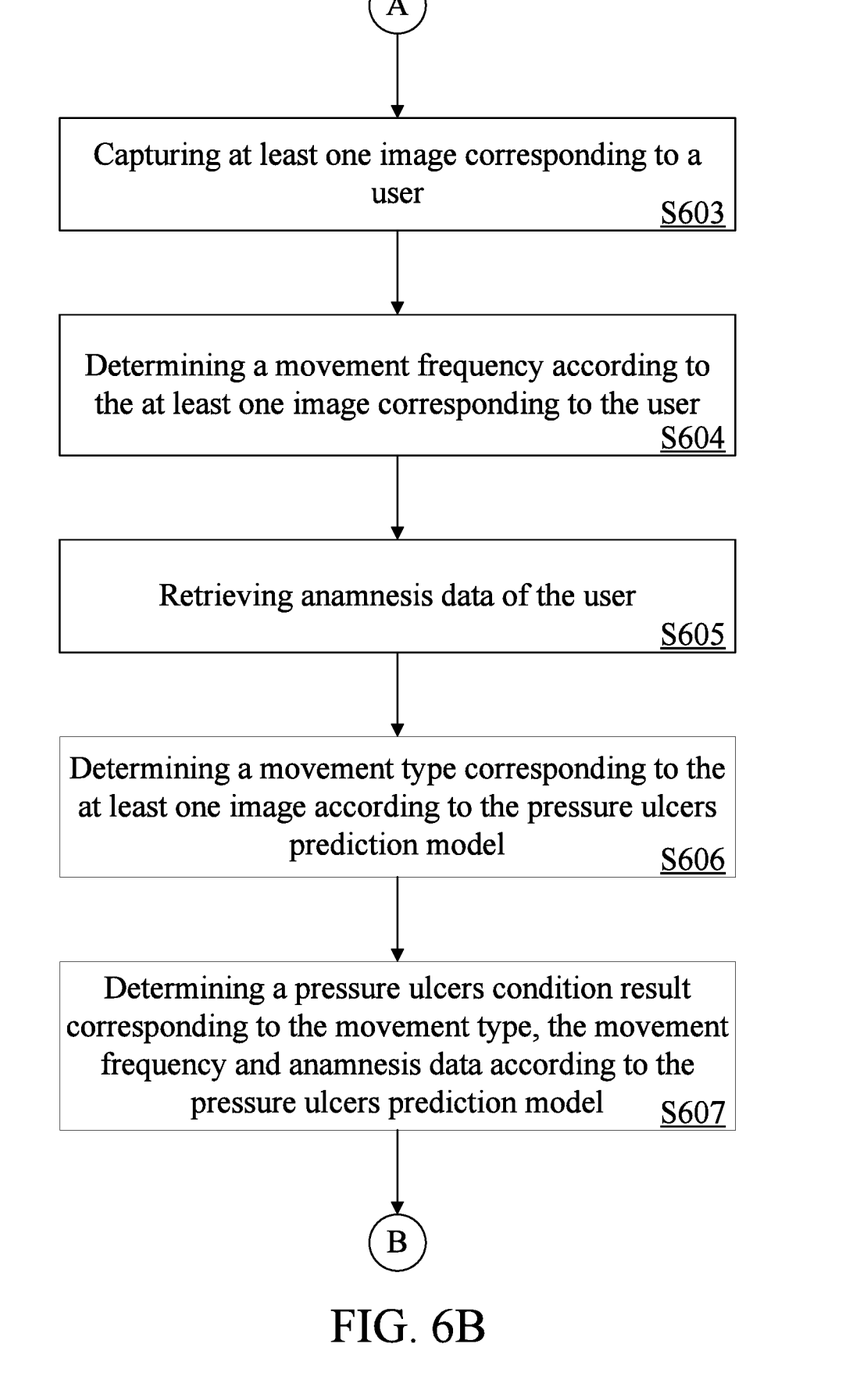
Figure 6C:
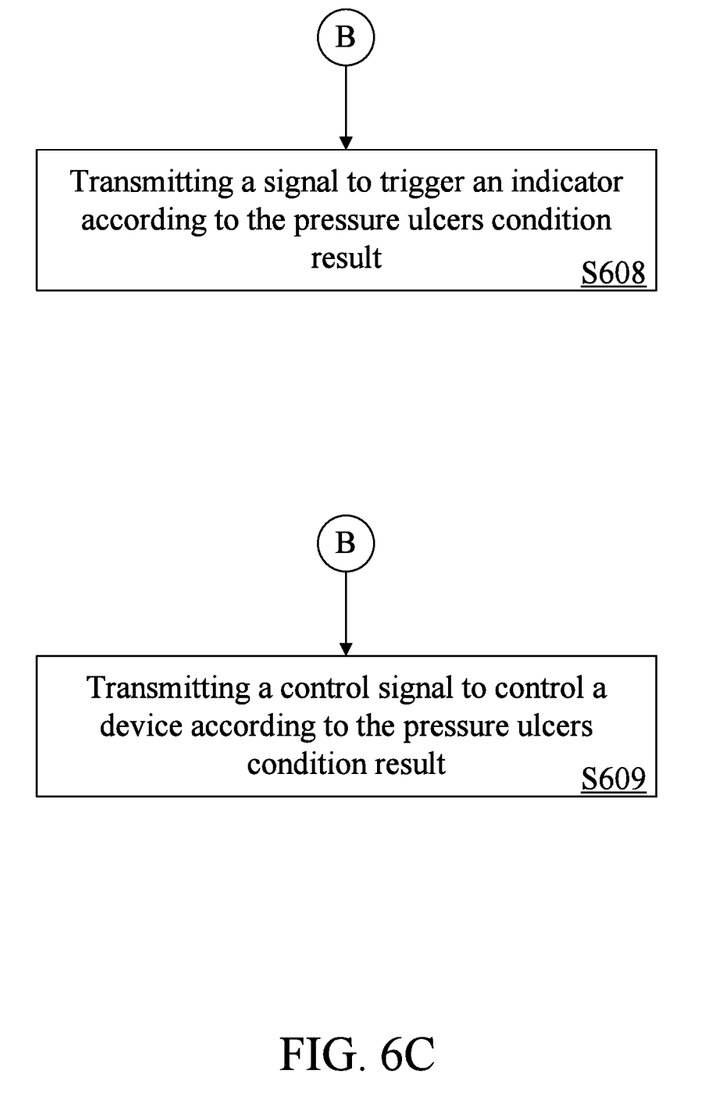

Some embodiments of the present disclosure include a computer-implemented method for monitoring pressure ulcers, and flowchart diagrams thereof are shown in FIGS. 6A to 6C. The computer-implemented method of some embodiments is for use in a monitoring system (e.g., the monitoring system 1 of the aforesaid embodiments). Detailed steps of the computer-implemented method are described below.

In some embodiments, a pressure ulcers prediction model may be generated and trained first before put to use. Step S601 is executed, by a processor of the monitoring system, to generate the pressure ulcers prediction model according to a machine learning scheme with training data of a plurality of first data and a plurality of second data.

In some embodiments, each first data includes a first training input data and a first training output data. The first training input data includes a plurality of training images. The first training output data includes a plurality of training movement types which corresponding to the training images.

During the generation of the pressure ulcers prediction model, the training images and the training movement types are used for training a first phase of the pressure ulcers prediction model to recognize images as movement type. In some embodiments, the movement type may include turning over, feeding, changing intravenous drip position, massaging, wound cleaning, or changing medical supply.

In some embodiments, each second data includes a second training input data and a second training output data. The second training input data includes a plurality of training movement types, a plurality of training movement frequencies and plurality of training anamnesis data. The second training output data includes a plurality of training pressure ulcers condition results.

During the generation of the pressure ulcers prediction model, the training movement types, the training movement frequencies, the training anamnesis data and the training pressure ulcers condition results are used for training a second phase of the pressure ulcers prediction model to determine pressure ulcers condition result according to movement type, movement frequency and anamnesis data.

After generating the pressure ulcers prediction model, step S602 is executed, by the processor, to store the pressure ulcers prediction model in a storing unit of the monitoring system for later use.

When a user needs to be monitored, step S603 is executed, by an image capturing unit, to capture at least one image corresponding to the user. Step S604 is executed, by the processor, to determine a movement frequency according to the at least one image corresponding to the user.

Step S605 is executed, by the processor, to retrieve anamnesis data of the user. The anamnesis data is stored in the storing unit of the monitoring system. In some embodiments, the anamnesis data is in text format and includes at least one of disease type information, prescription information, medical test information, blood pressure information and body temperature information.

Step S606 is executed, by the processor, to determine a movement type corresponding to the at least one image according to the pressure ulcers prediction model. Step S607 is executed, by the processor, to determine the pressure ulcers condition result corresponding to the movement type, the movement frequency and the anamnesis data according the pressure ulcers prediction model.

In some embodiments, step S608 is optionally executed, by the processor, to transmit a signal to trigger an indicator according to the pressure ulcers condition result. In some embodiments, step S609 is optionally executed, by the processor, to transmit a control signal to control a device according to the pressure ulcers condition result.

Figure 7:
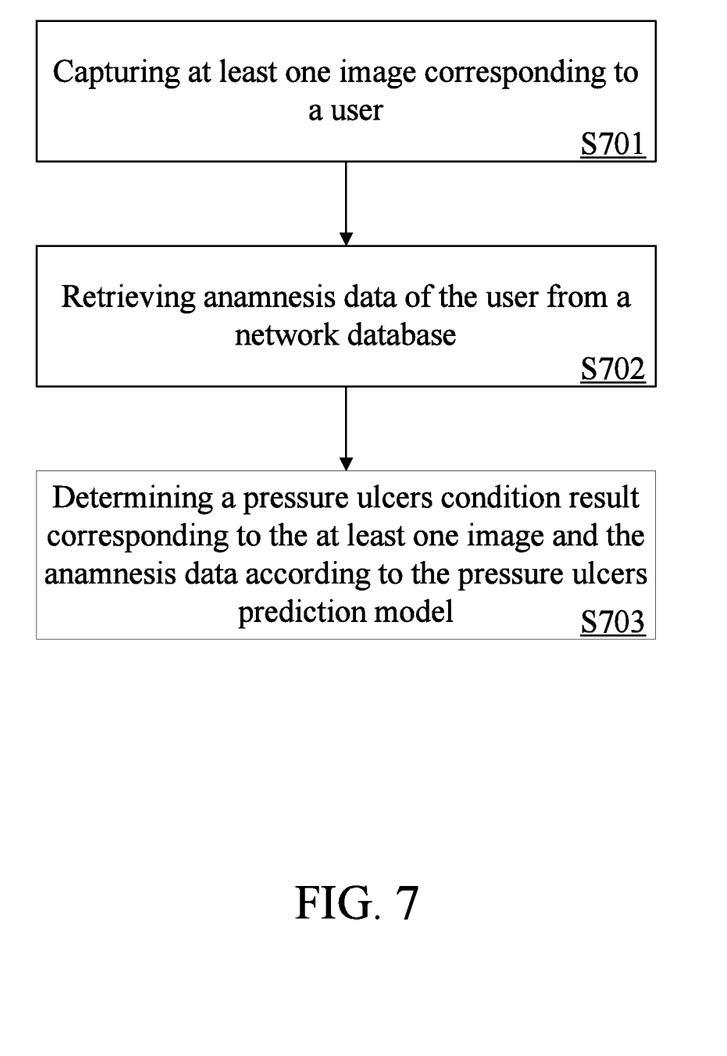
FIG. 7 is a flowchart diagram of a computer-implemented method for monitoring pressure ulcers according to some embodiments of the present disclosure.

Some embodiments of the present disclosure include a computer-implemented method for monitoring pressure ulcers, and a flowchart diagram thereof is shown in FIG. 7. The computer-implemented method of some embodiments is for use in a device (e.g., the device 4 of the aforesaid embodiments). Detailed steps of the computer-implemented method are described below.

Step S701 is executed, by an image capturing unit of the device, to capture at least one image corresponding to a user. Step S702 is executed, by a processor of the device, to retrieve anamnesis data of the user via a network interface of the device. The anamnesis data is stored in a network database.

In some embodiments, a pressure ulcers prediction model stored in the storing unit is a trained machine learning scheme that image data and anamnesis data corresponding to the user are inputted to the pressure ulcers prediction model, and subsequently pressure ulcers condition result is outputted from the pressure ulcers prediction model based on the inputted data.

Accordingly, Step S703 is executed, by the processor, to determine a pressure ulcers condition result corresponding to the at least one image and the anamnesis data according the pressure ulcers prediction model. The pressure ulcers condition result may include different levels for indicating different predictions of the pressure ulcers condition of the user.

It shall be particularly appreciated that the processors mentioned in the above embodiments may be a central processing unit (CPU), other hardware circuit elements capable of executing relevant instructions, or combination of computing circuits that are well-known by those skilled in the art based on the above disclosures.

Moreover, the storing units mentioned in the above embodiments may include memories, such as ROM, RAM, etc., or storing device, such as flash memory, HDD, SSD, etc., for storing data. Further, the communication buses mentioned in the above embodiments may include a communication interface (or I/O interface) for transferring data between the elements, such as the image capturing unit, the processor, the storing unit, the indicator and the device, and may include electrical bus interface, optical bus interface or even wireless bus interface. However, such description is not intended to limit the hardware implementation embodiments of the present disclosure.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A computer-implemented method for monitoring pressure ulcers, comprising:
    capturing, by an image capturing unit of a monitoring system, a plurality of images corresponding to a user;
    determining, by a processor of the monitoring system, a movement frequency according to the plurality of images corresponding to the user;
    retrieving, by the processor, anamnesis data of the user, wherein the anamnesis data is stored in a storing unit of the monitoring system; and
    determining, by the processor, a pressure ulcers condition result corresponding to the plurality of images and the anamnesis data according to a pressure ulcers prediction model stored in the storing unit,
    wherein the pressure ulcers prediction model is a machine learning model including a first phase and a second phase, the processor inputs the plurality of images to the first phase of the pressure ulcers prediction model for deriving a movement type from the first phase of the pressure ulcers prediction model, and the processor inputs the movement type, the movement frequency and the anamnesis data to the second phase of the pressure ulcers prediction model for deriving the pressure ulcers condition result from the second phase of the pressure ulcers prediction model.

2. The computer-implemented method of claim 1, further comprising:
    generating, by the processor, the pressure ulcers prediction model according to a machine learning scheme with training data of a plurality of first data and a plurality of second data, wherein the plurality of first data are used for training the first phase of the pressure ulcers prediction model to convert a plurality of training images into a plurality of training movement types, and the plurality of second data are used for training the second phase of the pressure ulcers prediction model to convert the plurality of training movement types, a plurality of training movement frequencies and a plurality of training anamnesis data into a plurality of pressure ulcers condition results,
    wherein:
        each first data includes a first training input data and a first training output data, the first training input data includes the plurality of training images, and the first training output data includes the plurality of training movement types; and
        each second data includes a second training input data and a second training output data, the second training input data includes the plurality of training movement types, the plurality of training movement frequencies and the plurality of training anamnesis data, and the second training output data includes the plurality of training pressure ulcers condition results.

3. The computer-implemented method of claim 1, wherein the movement type is at least one of turning over, feeding, changing intravenous drip position, massaging, wound cleaning, and changing medical supply.

4. The computer-implemented method of claim 1, wherein the anamnesis data is in text format and comprises at least one of disease type information, prescription information, medical test information, blood pressure information and body temperature information.

5. The computer-implemented method of claim 1, further comprising:
transmitting, by the processor, a signal to trigger an indicator according to the pressure ulcers condition result.

6. The computer-implemented method of claim 1, further comprising:
transmitting, by the processor, a control signal to control a device according to the pressure ulcers condition result.

7. The computer-implemented method of claim 1, wherein the pressure ulcers prediction model includes a self-learning machine learning model, and an input data to the pressure ulcers prediction model and an output data from the pressure ulcers prediction model are respectively used as a training input data and a training output data for training the pressure ulcers prediction model.

8. A monitoring system for monitoring pressure ulcers, comprising:
an image capturing unit for capturing a plurality of images corresponding to a user;
a processor; and
a storing unit for storing anamnesis data of the user, a pressure ulcers prediction model and a program that, when being executed, causes the processor to:
retrieve the plurality of images from the image capturing unit;
determine a movement frequency according to the plurality of images corresponding to the user;
retrieve the anamnesis data from the storing unit; and
determine a pressure ulcers condition result corresponding to the plurality of images and the anamnesis data according to the pressure ulcers prediction model, wherein the pressure ulcers prediction model is a machine learning model including a first phase and a second phase, the processor inputs the plurality of images to the first phase of the pressure ulcers prediction model for deriving a movement type from the first phase of the pressure ulcers prediction model, and the processor inputs the movement type, the movement frequency and the anamnesis data to the second phase of the pressure ulcers prediction model for deriving the pressure ulcers condition result from the second phase of the pressure ulcers prediction model.

9. The monitoring system of claim 8, wherein the program, when being executed, further causes the processor to:
generate the pressure ulcers prediction model according to a machine learning scheme with training data of a plurality of first data and a plurality of second data, wherein the plurality of first data are used for training the first phase of the pressure ulcers prediction model to convert a plurality of training images into a plurality of training movement types, and the plurality of second data are used for training the second phase of the pressure ulcers prediction model to convert the plurality of training movement types, a plurality of training movement frequencies and a plurality of training anamnesis data into a plurality of pressure ulcers condition results,
wherein:
each first data includes a first training input data and a first training output data, the first training input data includes the plurality of training images, and the first training output data includes the plurality of training movement types; and
each second data includes a second training input data and a second training output data, the second training input data includes the plurality of training movement types, the plurality of training movement frequencies and the plurality of training anamnesis data, and the second training output data includes the plurality of training pressure ulcers condition results.

10. The monitoring system of claim 8, wherein the movement type is at least one of turning over, feeding, changing intravenous drip position, massaging, wound cleaning, and changing medical supply.

11. The monitoring system of claim 8, wherein the anamnesis data is in text format and comprises at least one of disease type information, prescription information, medical test information, blood pressure information and body temperature information.

12. The monitoring system of claim 8, further comprising an indicator, wherein the program, when being executed, further causes the processor to transmit a signal to trigger the indicator according to the pressure ulcers condition result.

13. The monitoring system of claim 8, further comprising a device, wherein the program, when being executed, further causes the processor to transmit a control signal to control the device according to the pressure ulcers condition result.

14. A device, comprising:
a network interface for connecting with a network database;
an image capturing unit for capturing a plurality of images corresponding to a user;
a processor; and
a storing unit for storing a pressure ulcers prediction model and a program that, when being executed, causes the processor to:
retrieve the plurality of images from the image capturing unit;
determine a movement frequency according to the plurality of images corresponding to the user;
retrieve anamnesis data from the network database via the network interface; and
determine a pressure ulcers condition result corresponding to the plurality of images and the anamnesis data according to the pressure ulcers prediction model, wherein the pressure ulcers prediction model is a machine learning model including a first phase and a second phase, the processor inputs the plurality of images to the first phase of the pressure ulcers prediction model for deriving a movement type from the first phase of the pressure ulcers prediction model, and the processor inputs the movement type, the movement frequency and the anamnesis data to the second phase of the pressure ulcers prediction model for deriving the pressure ulcers condition result from the second phase of the pressure ulcers prediction model.

* * * * *